US008022179B2

(12) United States Patent
Dake et al.

(10) Patent No.: US 8,022,179 B2
(45) Date of Patent: Sep. 20, 2011

(54) COMPOSITIONS AND METHODS FOR TOPICAL APPLICATION AND TRANSDERMAL DELIVERY OF AN OLIGOPEPTIDE

(75) Inventors: Michael D. Dake, Stanford, CA (US); Jacob M. Waugh, Mountain View, CA (US)

(73) Assignee: Revance Therapeutics, Inc., Mountain View, CA (US)

( * ) Notice: Subject to any disclaimer, the term of this patent is extended or adjusted under 35 U.S.C. 154(b) by 464 days.

(21) Appl. No.: 11/368,198

(22) Filed: Mar. 3, 2006

(65) Prior Publication Data

US 2007/0037252 A1 Feb. 15, 2007

Related U.S. Application Data

(60) Provisional application No. 60/658,741, filed on Mar. 3, 2005.

(51) Int. Cl.
| | |
|---|---|
| A61K 38/08 | (2006.01) |
| A61K 38/10 | (2006.01) |
| A61K 31/74 | (2006.01) |
| A61K 39/08 | (2006.01) |
| C07K 4/00 | (2006.01) |

(52) U.S. Cl. ........... 530/326; 530/329; 424/78.02; 424/78.03; 424/247.1; 514/1.1; 514/21.8

(58) Field of Classification Search ............ 514/12, 514/17
See application file for complete search history.

(56) References Cited

U.S. PATENT DOCUMENTS

| | | | |
|---|---|---|---|
| 4,078,060 A | 3/1978 | Benson et al. | |
| 4,816,568 A | 3/1989 | Hamilton, Jr. et al. | |
| 5,512,547 A | 4/1996 | Johnson et al. | |
| 5,607,691 A | 3/1997 | Hale et al. | |
| 5,629,020 A | 5/1997 | Leone-Bay et al. | |
| 5,709,861 A | 1/1998 | Santiago et al. | |
| 5,744,166 A | 4/1998 | Illum | |
| 5,747,641 A | 5/1998 | Frankel et al. | |
| 5,756,468 A | 5/1998 | Johnson et al. | |
| 5,766,605 A | 6/1998 | Sanders et al. | |
| 5,795,587 A | 8/1998 | Gao et al. | |
| 5,804,604 A | 9/1998 | Frankel et al. | |
| 6,306,423 B1 | 10/2001 | Donovan et al. | |
| 6,312,708 B1 | 11/2001 | Donovan | |
| 6,383,509 B1 | 5/2002 | Donovan et al. | |
| 6,413,941 B1 | 7/2002 | Garnett et al. | |
| 6,495,663 B1 | 12/2002 | Rothbard et al. | |
| 6,506,399 B2 | 1/2003 | Donovan | |
| 6,585,993 B2 | 7/2003 | Donovan et al. | |
| 6,593,292 B1 | 7/2003 | Rothbard et al. | |
| 6,610,820 B1 | 8/2003 | Bonny | |
| 6,645,501 B2 | 11/2003 | Dowdy | |
| 6,669,951 B2 | 12/2003 | Rothbard et al. | |
| 6,680,301 B2 | 1/2004 | Berg et al. | |
| 6,683,049 B1 | 1/2004 | Aoki et al. | |
| 6,692,911 B2 | 2/2004 | Pack et al. | |
| 6,696,038 B1 * | 2/2004 | Mahato et al. | ............. 424/1.45 |
| 6,730,293 B1 | 5/2004 | Rothbard et al. | |
| 6,759,387 B2 | 7/2004 | Rothbard et al. | |
| 6,831,059 B2 | 12/2004 | Donovan | |
| 6,866,856 B2 | 3/2005 | Lu et al. | |
| 6,896,886 B2 | 5/2005 | Aoki et al. | |
| 6,974,578 B1 | 12/2005 | Aoki et al. | |
| 7,008,924 B1 | 3/2006 | Yan et al. | |
| 7,015,192 B1 * | 3/2006 | Mira et al. | .................. 514/2 |
| 7,056,656 B1 | 6/2006 | Rana et al. | |
| 7,060,498 B1 | 6/2006 | Wang | |
| 7,071,167 B2 * | 7/2006 | Renault | ..................... 514/17 |
| 2002/0009491 A1 | 1/2002 | Rothbard et al. | |
| 2002/0131965 A1 | 9/2002 | Rothbard et al. | |
| 2003/0022831 A1 | 1/2003 | Rothbard et al. | |
| 2003/0032593 A1 | 2/2003 | Wender et al. | |
| 2003/0083256 A1 | 5/2003 | Rothbard et al. | |
| 2003/0138437 A1 | 7/2003 | Hunt | |
| 2003/0162719 A1 | 8/2003 | Rothbard et al. | |
| 2003/0165567 A1 | 9/2003 | Mixson | |
| 2003/0185788 A1 | 10/2003 | Rothbard et al. | |
| 2003/0215395 A1 * | 11/2003 | Yu et al. | ................ 424/9.322 |
| 2003/0215412 A1 | 11/2003 | Waugh et al. | |
| 2003/0220480 A1 | 11/2003 | Bonny | |
| 2004/0009180 A1 | 1/2004 | Donovan | |
| 2004/0013687 A1 | 1/2004 | Simpson | |

(Continued)

FOREIGN PATENT DOCUMENTS

EP          1 180 524          2/2002

(Continued)

OTHER PUBLICATIONS

Dang, C.V., et al. 1989 The Journal of Biological Chemistry 264(30): 18019-18023.*

(Continued)

*Primary Examiner* — Marsha M Tsay
(74) *Attorney, Agent, or Firm* — Knobbe Martens Olson & Bear, LLP (57) ABSTRACT

The invention relates to the transdermal application of oligopeptides for reducing synaptic transmission in tissues of an animal. In one aspect, this invention relates to compositions comprising an oligopeptide and optionally a carrier comprising a positively charged "backbone" having positively charged branching or "efficiency" groups, as described herein. Most preferably the positively charged carrier is a long-chain positively charged polypeptide or a positively charged nonpeptidyl polymer, for example, a polyalkyleneimine. The invention further relates methods for producing a biologic effect of reducing synaptic transmission in a tissue by topically applying an effective amount of such a composition, preferably to the skin, of a subject or patient in need of such treatment. This invention also provides kits for preparing or formulating a composition that comprises the oligopeptide and optionally a carrier, as well as such additional items that are needed to produce a usable formulation, or a premix that may in turn be used to produce such a formulation.

26 Claims, 2 Drawing Sheets

U.S. PATENT DOCUMENTS

| | | | |
|---|---|---|---|
| 2004/0033241 | A1 | 2/2004 | Donovan |
| 2004/0037853 | A1 | 2/2004 | Borodic |
| 2004/0127556 | A1 | 7/2004 | Lu et al. |
| 2004/0147443 | A1 | 7/2004 | Renault |
| 2004/0161405 | A9 | 8/2004 | Rothbard et al. |
| 2004/0186045 | A1 | 9/2004 | Rothbard et al. |
| 2004/0192754 | A1 | 9/2004 | Shapira et al. |
| 2004/0220100 | A1 | 11/2004 | Waugh et al. |
| 2004/0220386 | A1 | 11/2004 | Steward et al. |
| 2004/0247614 | A1 | 12/2004 | Dorr et al. |
| 2004/0247623 | A1 | 12/2004 | Cady |
| 2005/0074461 | A1 | 4/2005 | Donovan |
| 2005/0112146 | A1 | 5/2005 | Graham |
| 2005/0175636 | A1 | 8/2005 | Donovan |
| 2005/0232966 | A1 | 10/2005 | Hughes |
| 2005/0238667 | A1 | 10/2005 | Hunt |
| 2006/0018931 | A1 | 1/2006 | Taylor |
| 2006/0024331 | A1 | 2/2006 | Fernandaz-Salazs et al. |
| 2006/0040882 | A1 | 2/2006 | Chen |

FOREIGN PATENT DOCUMENTS

| | | |
|---|---|---|
| EP | 1180524 | 2/2002 |
| RU | 2233665 C2 | 8/2004 |
| WO | WO 92/07871 | 5/1992 |
| WO | WO 94/04686 | 3/1994 |
| WO | 97/34620 | 9/1997 |
| WO | WO 97/40854 | 11/1997 |
| WO | WO 98/19710 | 5/1998 |
| WO | WO 00/32764 | 6/2000 |
| WO | WO 00/34308 | 6/2000 |
| WO | WO 01/13957 | 3/2001 |
| WO | WO 01/62297 | 8/2001 |
| WO | WO 02/07773 | 1/2002 |
| WO | WO 02/065986 | 8/2002 |
| WO | WO 02/067917 | 9/2002 |
| WO | WO 02/069930 | 9/2002 |
| WO | WO 03/049772 | 6/2003 |
| WO | WO 03/072049 | 9/2003 |
| WO | WO 03/097107 | 11/2003 |

OTHER PUBLICATIONS

Voet et al., Biochemistry, Second Edition, John Wiley and Sons, Inc., pp. 1275-1276, 1995.

Kalderon et al. A Short Amino Acid Sequence Able to Specify Nuclear Location, Cell, vol. 39, pp. 499-509, 1984.

Blanes-Mira et al., "Identification of SNARE Complex Modulators that Inhibit Exocytosis from an Alpha-Helix-Constrained Combinatorial Library", Biochem. J., vol. 375, No. 1, pp. 159-166, Oct. 1, 2003.

Blanes-Mira et al., "Small Peptides Patterned After the N-Terminus Domain of SNAP25 Inhibit SNARE Complex Assembly and Regulated Exocytosis", J. of Neurochem., vol. 88, No. 1, pp. 124-135, Jan. 2004.

Blanes-Mira et al., "A Synthetic Hexapeptide (Argireline) with Antiwrinkle Activity", Int'l J. of Cosmetic Science, vol. 24, No. 5, pp. 303-310, 2002.

PCT Search Report dated Nov. 15, 2006.

Yano et al., "Control of Hair Growth and Follicle Size by VEGF-Mediated Angiogensis," J. Clin. Invest., 107:409-417, 2001.

Morris et al., "A Peptide Carrier for the Delivery of Biologically Active Proteins into Mammalian Cells," Nature Biotechnology, vol. 19, Dec. 1, 2001, pp. 1173-1176.

"AIDS, Use of HIV-1 TAT, to target and/or activate antigen-presenting cells, and/or to deliver cargo molecules" from http://pharmalicensing.com/public/outlicensing/view/3766 (2001).

Green, M. "Mutational analysis of HIV-1 TAT minimal domain peptides: identification of trans-dominant mutants that suppress HIV-LTR-driven gene expression", Cell, 58:215-223, 1989.

Blanes-Mira et al., "Identification of SNARE Complex Modulators that Inhibit Exocytosis from an Alpha-Helix-Constrained Combinatorial Library," Biochem. J., vol. 375, No. 1, pp. 159-166, Oct. 1, 2003.

Blanes-Mira et al., "Small Peptides Patterned After the N-Terminus Domain of SNAP25 Inhibit SNARE Complex Assembly and Regulated Exocytosis," J. of Neurochem., vol. 88, No, 1, pp. 124-135, Jan. 2004.

Blanes-Mira et al., "A Synthetic Hexapeptide (Argireline) with Antiwrinkle Activity," Int'l J. of Cosmetic Science, vol. 24, No. 5, pp. 303-310, 2002.

Fisher et al., "Matrix Sialoprotein of Develping Bone," J. Biol. Chem., vol. 258, pp. 12723-12727, Oct. 1983.

http:www.genlantis.com/catalog/product_line.cfm?product_family_key=13&product_line_key=54, retrieved from the internet on Sep. 2, 2005.

* cited by examiner

SEQUENCE LISTING

<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Glu Met Gln Arg Arg
1               5

<210> SEQ ID NO 2
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 2

Asp Asp Asp Asp Glu Glu Met Gln Arg Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Glu Met Gln Arg Arg Asp Asp Asp Asp
1               5                   10

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 residues
<220> FEATURE:
<221> NAME/KEY: MOD_RES
<222> LOCATION: (21)..(45)
<223> OTHER INFORMATION: This region may encompass an odd integer of
      5-25 residues
<220> FEATURE:
<223> OTHER INFORMATION: See specification as filed for detailed
      description of substitutions and preferred embodiments

<400> SEQUENCE: 4

Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45

<210> SEQ ID NO 5
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 residues
<220> FEATURE:
<221> NAME/KEY: MOD_RES
<222> LOCATION: (32)..(51)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 5

Gly Gly Gly Gly Gly Gly Gly Gly Gly Gly Gly Gly Gly Gly Gly Gly
1               5                   10                  15
```

```
Gly Gly Gly Gly Arg Gly Arg Asp Asp Arg Arg Gln Arg Arg Gly
            20                  25                  30

Gly Gly Gly Gly Gly Gly Gly Gly Gly Gly Gly Gly Gly Gly Gly
            35                  40                  45

Gly Gly Gly
    50

<210> SEQ ID NO 6
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 residues
<220> FEATURE:
<221> NAME/KEY: MOD_RES
<222> LOCATION: (32)..(51)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 6

Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Gly
            20                  25                  30

Gly Gly Gly Gly Gly Gly Gly Gly Gly Gly Gly Gly Gly Gly Gly
            35                  40                  45

Gly Gly Gly
    50

<210> SEQ ID NO 7
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(20)
<223> OTHER INFORMATION: This region may encompass 0-20 residues
<220> FEATURE:
<221> NAME/KEY: MOD_RES
<222> LOCATION: (30)..(49)
<223> OTHER INFORMATION: This region may encompass 0-20 residues
<220> FEATURE:
<223> OTHER INFORMATION: See specification as filed for detailed
      description of substitutions and preferred embodiments

<400> SEQUENCE: 7

Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Gly Gly Gly
            20                  25                  30

Gly Gly Gly Gly Gly Gly Gly Gly Gly Gly Gly Gly Gly Gly Gly
            35                  40                  45

Gly

<210> SEQ ID NO 8
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Arg Arg Arg Arg Arg Arg Arg
1               5                   10
```

COMPOSITIONS AND METHODS FOR TOPICAL APPLICATION AND TRANSDERMAL DELIVERY OF AN OLIGOPEPTIDE

This application claims benefit of priority of U.S. Provisional Application Ser. No. 60/658,741 filed Mar. 3, 2005, incorporated herein by reference in its entirety.

FIELD OF THE INVENTION

The invention relates to the transdermal application of oligopeptides for reducing synaptic transmission in tissues of an animal.

BACKGROUND OF THE INVENTION

This invention relates to new compositions comprising an oligopeptide, more specifically to such compositions that enable the transport or delivery of an oligopeptide through the skin or epithelium (also referred to as "transdermal delivery"), and that therefore may be used as topical applications for providing an oligopeptide to a subject, for various therapeutic, aesthetic and/or cosmetic purposes, as described herein.

Botulinum toxins (also known as botulin toxins or botulinum neurotoxins) are neurotoxins produced by the gram-positive bacteria *Clostridium botulinum*. They act to produce paralysis of muscles by preventing synoptic transmission or release of acetylcholine across the neuromuscular junction, and are thought to act in other ways as well. Their action essentially blocks signals that normally would cause muscle spasms or contractions, resulting in paralysis.

Allan B. Scott first used botulinum toxin A (BTX-A) in monkeys in 1973. Scott demonstrated reversible ocular muscle paralysis lasting 3 months (Lamanna, *Science*, 130: 763-772 (1959)). Soon afterwards, BTX-A was reported to be a successful treatment in humans for strabismus, blepharospasm, and spasmodic torticollis (Baron et al. In: Baron E J, Peterson L R. Finegold S M (Eds), *Bailey & Scotts Diagnostic Microbiology*, St. Louis, Mo.: Mosby Year Book, 504-523 (1994); Carruthers and Carruthers, *Adv Dermatol*, 12:325-348 (1997); Markowitz, In: Strickland GT (Eds) *Hunters Tropical Medicine*, 7$^{th}$ ed. Philadelphia: W.B. Saunders. 441-444 (1991)). In 1986, Jean and Alastair Carruthers, a husband and wife team consisting of an ocuplastic surgeon and a dermatologist, began to evolve the cosmetic use of BTX-A for treatment of movement-associated wrinkles in the glabella area (Schantz and Scott, In Lewis GE (Ed) *Biomedical Aspects of Botulinium*. New York: Academic Press. 143-150 (1981)). The Carruthers' use of BTX-A for the treatment of wrinkles led to their seminal publication of this approach in 1992 (Schantz and Scott. In Lewis GE (Ed) *Biomedical Aspects of Botulinum*. New York: Academic Press. 143-150 (1992)). By 1994, the same team reported experiences with other movement-associated wrinkles on the face (Scott, *Ophthalmol*, 87:1044-1049 (1980)). This in turn led to the birth of the era of cosmetic BTX-A treatment.

Skin protects the body's organs from external environmental threats and acts as a thermostat to maintain body temperature. It consists of several different layers, each with specialized functions. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: *People's Medical Society*, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the horny layer loses its softness and flexibility it becomes rough and brittle, resulting in dry skin.

The dermis, which lies just beneath the epidermis, is 1.5 to 4 millimeters thick. It is the thickest of the three layers of the skin. In addition, the dermis is also home to most of the skin's structures, including sweat and oil glands (which secrete substances through openings in the skin called pores, or comedos), hair follicles, nerve endings, and blood and lymph vessels (Inlander, Skin, New York, N.Y.: *People's Medical Society*, 1-7 (1998)). However, the main components of the dermis are collagen and elastin.

The hypodermis is the deepest layer of the skin. It acts both as an insulator for body heat conservation and as a shock absorber for organ protection (Inlander, Skin, New York, N.Y.: *People's Medical Society*, 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

One of the principal functions of skin is to provide a barrier to the transportation of water and substances potentially harmful to normal homeostasis. The body would rapidly dehydrate without a tough, semi-permeable skin. The skin helps to prevent the entry of harmful substances into the body. Although most substances cannot penetrate the barrier, a number of strategies have been developed to selectively increase the permeability of skin with variable success.

Botulinum toxin type A is said to be the most lethal natural biological agent known to man. At the same time, the muscle-paralyzing effects of botulinum toxin have been used for therapeutic effects. Controlled administration of botulinum toxin has been used to provide muscle paralysis to treat conditions, for example, neuromuscular disorders characterized by hyperactive skeletal muscles. Conditions that have been treated with botulinum toxin include hemifacial spasm, adult onset spasmodic torticollis, anal fissure, blepharospasm, cerebral palsy, cervical dystonia, migraine headaches, strabismus, temperomandibular joint disorder, and various types of muscle cramping and spasms. More recently the muscle-paralyzing effects of botulinum toxin have been taken advantage of in therapeutic and cosmetic facial applications such as treatment of wrinkles, frown lines, and other results of spasms or contractions of facial muscles.

In all treatments currently used, the botulinum toxin is administered by carefully controlled or monitored injection, creating large wells of toxin at the treatment site. A few scattered references to topical treatment are present in the literature. For example, assertions that botulinum toxin may be applied topically are made in U.S. Pat. No. 6,063,768 of Eric R. First, but no information is given as to how this may be accomplished. In another patent in which First is named as an inventor. U.S. Pat. No. 6,087,327 (of Pearce and First), mention is made that the botulinum toxin may be topically administered by solubilization in normal phosphate buffer containing gelatin stabilizer and administered topically into the nasal cavity of a dog. The patent cites a publication by Shaari et al. (*Otolaryngol. Head Neck Surg.* 2; 566, 1995) in which such an experiment was conducted. German published patent application 198 52 981 describes topical compositions containing botulinum toxin and dimethyl sulfoxide for treatment of hyperhidrosis. An example in which a single patient was treated is included.

U.S. Pat. No. 5,670,484 (Binder) describes the use of botulinum toxin in treating cutaneous cell-proliferative disorders (for example, psoriasis and dermatitis) using neurotoxins, including botulinum toxin. The patent asserts that compositions may be applied topically, but no examples of suitable formulations are given, and in the test examples the botulinum toxin was administered by injection. U.S. published application 2003/0113349 (Coleman III) represents that topical formulations containing botulinum toxin may be used to treat hyperactive glandular conditions in the skin. However, the description relates to conditions in cutaneous glands and does not discuss transdermal applications. In addition, like most of the publications discussed here, it contains no working examples. Finally, U.S. published application 2004/0009180 (Donovan) discloses the use of botulinum toxin in topical treatments for a number of conditions, some of which apparently involve transdermal delivery, for instance, topical application to relax muscles. The publication states that transdermal delivery is accomplished by use of an enhancing agent. Agents said to be suitable for this purpose include various alcohols, including polyalcohols, amines, amides, transferomes and liposomes. The examples are all written in the present tense, indicating that some or all may be conceptual rather than empirical.

One approach to solving the problems associated with botulinum toxin therapy is to use fragments of the toxin or other agents that interfere with the SNARE complex. The SNARE complex is an assembly of three proteins that plays a central role in neuronal exocytosis, the process where neurotransmitter loaded vesicles fuse with the neuron cell membrane and expel their contents. (Gutierrez, L. M., et. al. *FEBS Lett.* 372, 39-43 (1995); Gutierrez, L. M., et. al. *J. Biol. Chem.* 272, 2634-2639 (1997); Ferrer-Montiel, A. V., et. al. *FEBS Lett.* 435, 84-88 (1998))

This work has resulted in identification of effective oligopeptides of 20 or more amino acids. However, these agents like botulinum toxins themselves were also found to have extremely poor ability to penetrate skin. More recently, a 6 amino acid peptide with the sequence glutamic acid-glutamic acid-methionine-glutamine-arginine-arginine (EEMQRR (SEQ ID NO: 1)) has been shown to retain some activity in one model. (C. Blanes-Mira, et. al. *International Journal of Cosmetic Science*, 2002, 24, 303-310).

This hexapeptide, when derivatized to improve skin penetration and employed at very high concentrations such as 10% affords wrinkle reduction in certain cases (acetyl hexapeptide or ARGIRELINE®). However, the transdermal penetration of this peptide even when derivatized with palmitate or acylated as in ARGIRELINE® remains so low that efficacy in wrinkle reduction requires high concentrations of expensive compounds-most of which does not cross the skin. Safety advantages relative to complete botulinum toxins are likely but have yet to be established in these applications given with the high load necessitated by low skin penetration. Hence, the limitations of botulinum toxins in terms of route of administration are largely preserved with these agents.

BRIEF SUMMARY OF THE INVENTION

It is apparent that there are at least two problems associated with the therapeutic use of botulinum toxin. The first is the inherent toxicity of botulinum toxin resulting in the requirement for close medical supervision of it's use. The second is the great difficulty in getting the botulinum toxin to penetrate the skin so it can reach the site where it is needed to exert it's biological effects. The present invention addresses both of these problems by providing an oligopeptide which has similar biological activity to botulinum toxin but with a much lower level of toxicity and a lower molecular weight to enhance its penetration of the skin.

In one aspect, this invention relates to compositions comprising an oligopeptide and optionally a carrier comprising a positively charged "backbone" having positively charged branching or "efficiency" groups, as described herein. Most preferably the positively charged carrier is a long-chain positively charged polypeptide or a positively charged nonpeptidyl polymer, for example, a polyalkyleneimine. The invention further relates methods for producing a biologic effect of reducing synaptic transmission in a tissue by topically applying an effective amount of such a composition, preferably to the skin, of a subject or patient in need of such treatment.

This invention also provides kits for preparing or formulating a composition that comprises the oligopeptide and optionally a carrier, as well as such additional items that are needed to produce a usable formulation, or a premix that may in turn be used to produce such a formulation. Alternatively the kit comprises means for separately, but in conjunction, administering the oligopeptide and a carrier to a subject.

This invention also provides a composition comprising a first oligopeptide of from 6 to about 20 amino acids, said first oligopeptide comprising the amino acid sequence of SEQ ID NO: 1, the composition further comprising a carrier comprising a second oligopeptide having attached positively charged branching groups independently selected from $-(gly)_{n1}-(arg)_{n2}$ (SEQ ID NO: 4), HIV-TAT, Antennapedia PTD, and fragments of HIV-TAT or of Antennapedia PTD or mixtures thereof, in which the subscript n1 is an integer of from 0 to about 20, and the subscript n2 is independently an odd integer of from about 5 to about 25.

This invention also provides a method for reducing symptoms associated with a medical condition selected from the list consisting of dystonia, muscle spasms, autonomic nerve disorders, cerebrel palsy, Parkinson's disease, tremors, epilepsy, inner ear disorders, muscles disorders, nerve entrapment disorders, hyperhidrosis, acne, mucous, secretions, psoriasis, diabetes related cutaneous disorders, wound healing, mammary gland disorders, hair growth, urologic disorders, neuropshychiatric disorders, cancer and hypercalcemia comprising administering a therapeutically effective amount of the composition comprising a first oligopeptide of from 6 to about 20 amino acids, said first oligopeptide comprising the amino acid sequence of SEQ ID NO: 1, the composition further comprising a carrier comprising a second oligopeptide having attached positively charged branching groups independently selected from $-(gly)_{n1}-(arg)_{n2}$ (SEQ ID NO: 4), HIV-TAT, Antennapedia PTD, and fragments of HIV-TAT or of Antennapedia PTD or mixtures thereof, in which the subscript n1 is an integer of from 0 to about 20, and the subscript n2 is independently an odd integer of from about 5 to about 25.

This invention also provides a compound comprising an oligopeptide of from 7 to about 20 amino acids, said oligopeptide comprising the amino acid sequence of SEQ ID NO: 1. In some embodiments the oligopeptide may comprise from 8, 9 or 10 to about 20 amino acids.

This invention also provides a method for reducing symptoms associated with a medical condition selected from the list consisting of dystonia, muscle spasms, autonomic nerve disorders, cerebrel palsy, Parkinson's disease, tremors, epilepsy, inner ear disorders, muscles disorders, nerve entrapment disorders, hyperhidrosis, acne, mucous, secretions, psoriasis, diabetes related cutaneous disorders, wound healing, mammary gland disorders, hair growth, urologic disorders, neuropshychiatric disorders, cancer and hypercalcemia comprising administering a therapeutically effective amount of a compound comprising an oligopeptide of from 7 to about 20 amino acids, said oligopeptide comprising the amino acid sequence of SEQ ID NO: 1.

DETAILED DESCRIPTION OF THE INVENTION

This invention provides compositions and methods for delivery, particularly transdermal delivery, of an oligopeptide by topical application of an appropriate formulation.

The oligopeptide comprises from 6 to about 20 amino acids and comprises the amino acid sequence EEMQRR (SEQ ID NO: 1). As the oligopeptide is to be delivered transdermally, it is preferred that the oligopeptide comprise as few amino acids beyond 6 as possible, with a maximum size of approximately 20 amino acids. In some embodiments the oligopeptide comprises from either 7, 8, 9 or 10 to about 20 amino acids and comprises the amino acid sequence EEMQRR (SEQ ID NO: 1). The amino acids may be in either the D or L form. To enhance transdermal delivery, this oligopeptide may be optionally modified by the addition of charged groups including but not limited to an acetyl group, an amide group, a phosphate group, or fatty acids including but not limited to a palmitoyl group or similar such modifications. In some embodiments, the oligopeptide contains a sequence of 3-14 neutral or non-polar amino acids immediately adjacent to SEQ ID NO: 1 so as to provide an amphipathic character to the oligopeptide, enhancing its ability to penetrate the skin. These modifications of the oligopeptide may be at either the C-terminal or N-terminal end of the oligopeptide or at both ends. Modifications may also be combined on one oligopeptide, as a non-limiting example the oligopeptide could be acetylated at the N-terminal end and contain neutral amino acids at the C-terminal end or the reverse. Oligopeptides with different modifications could also be combined in some embodiments.

For embodiments where the oligopeptide is to be used together with a positively charged carrier, the oligopeptide may contain amino acid sequences adjacent to SEQ ID NO: 1 which enhance the non-covalent interaction between the oligopeptide and positively charged carrier. For example sequences of acidic, negatively charged amino acids would interact strongly with the positively charged carrier. Two non-limiting embodiments of such an oligopeptide are the decapeptides DDDDEEMQRR (SEQ ID NO: 2) and EEMQRRDDDD (SEQ ID NO: 3). In some embodiments, mixtures of different oligopeptides may be used, for example both of the decapeptides SEQ ID NO: 2 and SEQ ID NO: 3 could be used in combination.

The amino acid sequence SEQ ID NO: 1 of the oligopeptide interferes with the functioning of the SNARE complex in a manner similar to botulinum toxin resulting in the inhibition of the release of acetylcholine and a resultant decrease in synaptic transmission. SEQ ID NO: 1 has been shown to have biological effects similar to botulinum toxin (C. Blanes-Mira, et. al. *International Journal of Cosmetic Science*, 2002, 24, 303-310).

Given the ability of SEQ ID NO: 1 to reduce synaptic transmission, there are a number of medical conditions which could be treated with this oligopeptide. These include but are not limited to conditions where chronic muscle contractions or spasms cause pain or disability. Such conditions include but are not limited to migraine or other headaches, cerebral palsy, Parkinson's disease, epilepsy, tremors, dystonias, muscle spasms, autonomic nerve disorders, strabismus and palatal myoclonus. Without being limited by theory, administration of the oligopeptide of the present invention would block or reduce the nerve impulses reaching the affected muscles thereby ameliorating or alleviating the condition. The present invention is not intended to improve cosmetic appearance by reducing or eliminating fine lines or wrinkles of the face.

The oligopeptide of the present invention could also be used to treat a variety of glandular conditions. Many glandular tissues are controlled by autonomic nerve impulses and the oligopeptide of the present invention could be used to block these nerve impulses and thereby reduce secretion from these tissues. Specific medical conditions that would benefit from this treatment include but are not limited to hyperhidrosis, acne, seborrhiec dermatitis, mammary gland disorders and excess mucous secretion.

While the mechanism is not clear, neurotoxic compounds with activity on the SNARE complex similar to that of the oligopeptide of the present invention have been found to have activity in certain proliferative skin disorders such as psoriasis, cutaneous manifestations of diabetes and wound healing. Treatment with the oligopeptide of the present invention is expected to reduce or ameliorate the symptoms of proliferative skin disorders.

According to the present invention, a positively charged carrier molecule having efficiency groups, as described herein, has been found suitable as a transport system for an oligopeptide, enabling the oligopeptide to be administered transdermally to muscles and/or other skin-associated structures. The transport occurs without covalent modification of the oligopeptide.

By "positively charged" is meant that the carrier has a positive charge under at least some solution-phase conditions, including at least some physiologically compatible conditions. More specifically, "positively charged" as used herein, means that the group in question contains functionalities that are charged under all pH conditions, for instance, a quaternary amine, or contains a functionality which can acquire positive charge under certain solution-phase conditions, such as pH changes in the case of primary amines. More preferably, "positively charged" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art.

Generally, the positively-charged carrier (also referred to as a "positively charged backbone") is typically a linear chain of atoms, either with groups in the chain carrying a positive charge at physiological pH, or with groups carrying a positive charge attached to side chains extending from the backbone.

Preferably, the positively charged backbone itself will not have a defined enzymatic or therapeutic biologic activity. The linear backbone is a hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homo-polymer such as a polyalkyleneimine, for example a polyethyleneimine or polypropyleneimine, having a molecular weight of from about 10,000 to about 2,500,000, preferably from about 100,000 to about 1,800,000, and most preferably from about 500,000 to about 1,400,000. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. In all aspects of the present invention, the association between the carrier and the oligopeptide is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight of from about 10,000 to about 1,500,000, more preferably from about 25,000 to about 1,200,000, most preferably from about 100,000 to about 1,000,000. One of skill in the art will appreciate that when amino acids are used in this portion of the invention, the sidechains can have either the D- or L-form (R or S configuration) at the center of attachment. Alternatively, the backbone can be an analog of a polypeptide such as a peptoid. See, for example, Kessler, *Angew. Chem. Int. Ed. Engl.* 32:543 (1993); Zuckermann et al. *Chemtracts-Macromol. Chem.* 4:80 (1992); and Simon et al. *Proc. Nat'l Acad. Sci. USA* 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the α-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, ketomethylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) *Chem. Rev.* 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

In one embodiment, the positively charged backbone is a polypeptide having branching groups (also referred to as efficiency groups). As used herein, an efficiency group or branching group is any agent that has the effect of promoting the translocation of the positively charged backbone through a tissue or cell membrane. Non-limiting examples of branching or efficiency groups include -(gly)$_{n1}$, -(arg)$_{n2}$ (SEQ ID NO: 4), HIV-TAT or fragments thereof, or the protein transduction domain of Antennapedia, or a fragment thereof, in which the subscript n1 is an integer of from 0 to 20, in some embodiments 0 to 8, in other embodiments 2 to 5, and the subscript n2 is independently an odd integer of from about 5 to about 25, in some embodiments about 7 to about 17, in other embodiments about 7 to about 13. Further embodiments are those in which the HIV-TAT fragment has the formula (gly)$_p$-RGRDDRRQRRR-(gly)$_q$ (SEQ ID NO: 5), (gly)$_p$-YGRKKRRQRRR-(gly)$_q$ (SEQ ID NO: 6) or (gly)$_p$-RKKRRQRRR-(gly)$_q$ (SEQ ID NO: 7) wherein the subscripts p and q are each independently an integer of from 0 to 20 and the fragment is attached to the backbone via either the C-terminus or the N-terminus of the fragment. Preferred HIV-TAT fragments are those in which the subscripts p and q are each independently integers of from 0 to 8, more preferably 2 to 5. In another embodiment, the positively charged side chain or branching group is the Antennapedia (Ant) protein transduction domain (PTD), or a fragment thereof that retains activity. The positively charged carrier may also include sidechain positively charged branching groups in an amount of at least about 0.05%, as a percentage of the total carrier weight, from about 0.05 to about 45 weight %, and in some embodiments from about 0.1 to about 30 weight %. For positively charged branching groups having the formula -(gly)$_{n1}$-(arg)$_{n2}$, the amount is from about 0.1 to about 25%.

In another embodiment, the backbone portion is a polylysine and positively charged branching groups are attached to the lysine sidechain amino groups. The polylysine may have a molecular weight of from about 10,000 to about 1,500,000, in some embodiments from about 25,000 to about 1,200,000, and in other embodiments from about 100,000 to about 1,000, 000. It can be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and provide a length that is from one to four times the combined length of the negatively charged components. Suitable positively charged branching groups or efficiency groups include, for example, -gly-gly-gly-arg-arg-arg-arg-arg-arg-arg ($-Gly_3Arg_7$) (SEQ ID NO: 8) or HIV-TAT. In another embodiment the positively charged backbone is a long chain polyalkyleneimine such as a polyethyleneimine, for example, one having a molecular weight of about 1,000,000.

The positively charged backbones or carrier molecules comprising polypeptides or polyalkyleneimines, having the branching groups described above, are novel compounds and form an aspect of this invention.

In one embodiment of the invention, only a positively charged carrier that has positively charged branching groups is necessary for transdermal delivery of the botulinum toxin. In certain embodiments, the positively charged carrier is a polypeptide (e.g., lysine, arginine, ornithine, homoarginine, and the like) having multiple positively charged side-chain groups, as described above. The polypeptide has a molecular weight of at least about 10,000. In another embodiment, the positively charged carrier is a nonpeptidyl polymer such as a polyalkyleneimine having multiple positively charged side-chain groups having a molecular weight of at least about 100,000. Such polyalkyleneimines include polyethylene- and polypropyleneimines. In either instance, for use as the sole necessary agent for transdermal delivery the positively charged carrier molecule includes positively charged branching or efficiency groups, comprising $-(gly)_{n1}-(arg)_{n2}$ (SEQ ID NO: 4), in which the subscript n1 is an integer of from 0 to 20 in some embodiments 0 to 8, still other embodiments 2 to 5, and the subscript n2 is independently an odd integer of from about 5 to about 25, in some embodiments from about 7 to about 17, and other embodiments from about 7 to about 13, HIV-TAT or fragments thereof, or Antennapedia PTD or a fragment thereof. The side-chain or branching groups have the general formula $-(gly)_{n1}-(arg)_{n2}$ (SEQ ID NO: 4) as described above. Other embodiments are those in which the branching or efficiency groups are HIV-TAT fragments that have the formula $(gly)_p$-RGRDDRRQRRR-$(gly)_q$ (SEQ ID NO: 5), $(gly)_p$-YGRKKRRQRRR-$(gly)_q$ (SEQ ID NO: 6), or $(gly)_p$-RKKRRQRRR-$(gly)_q$ (SEQ ID NO: 7) wherein the subscripts p and q are each independently an integer of from 0 to 20 and the fragment is attached to the carrier molecule via either the C-terminus or the N-terminus of the fragment. The side branching groups can have either the D- or L-form (R or S configuration) at the center of attachment. Suitable HIV-TAT fragments are those in which the subscripts p and q are each independently integers of from 0 to 8, in some embodiments 2 to 5. Other embodiments are those in which the branching groups are Antennapedia PTD groups or fragments thereof that retain the group's activity. These are known in the art, for instance, from Console et al., *J. Biol. Chem.* 278: 35109 (2003). The positively charged carrier includes side-chain positively charged branching groups in an amount of at least about 0.05%, as a percentage of the total carrier weight, from about 0.05 to about 45 weight %, and other embodiments from about 0.1 to about 30 weight %. For positively charged branching groups having the formula-$(gly)_{n1}$-$(arg)_{n2}$, the amount is from about 0.1 to about 25%.

In another embodiment, the carrier is a polylysine with positively charged branching groups attached to the lysine side-chain amino groups. The polylysine used in this particularly embodiment can be any of the commercially available (Sigma Chemical Company, St. Louis, Mo., USA, e.g.) polylysines such as, for example, polylysine having MW>70,000, polylysine having MW of 70,000 to 150,000, polylysine having MW 150,000 to 300,000 and polylysine having MW>300,000. However, a suitable polylysine has a MW of at least about 10,000. Suitable positively charged branching groups or efficiency groups include, for example, -gly-gly-gly-arg-arg-arg-arg-arg-arg-arg ($-Gly_3Arg_7$) (SEQ ID NO: 8), HIV-TAT or fragments of it, and Antennapedia PTD or fragments thereof.

In other embodiments of this invention, the carrier is a relatively short polylysine or polyethyleneimine (PEI) backbone (which may be linear or branched) and which has positively charged branching groups. Such carriers are useful for minimizing uncontrolled aggregation of the backbones and botulinum toxin in a therapeutic composition, which causes the transport efficiency to decrease dramatically. When the carrier is a relatively short linear polylysine or PEI backbone, the backbone will have a molecular weight of less than 75,000, in some embodiments less than 30,000, and in other embodiments, less than 25,000. When the carrier is a relatively short branched polylysine or PEI backbone, however, the backbone will have a molecular weight less than 60,000, in some embodiments less than 55,000, and in other embodiments less than 50,000. If, however, partitioning agents as described herein are included in the composition, the molecular weight of the branched polylysine and PEI backbones may be up to 75,000, while the molecular weight of the linear polylysine and PEI backbones may be up to 150,000.

Compositions of this invention are in the form of products to be applied to the skin or epithelium of subjects or patients, i.e. humans or other mammals in need of the particular treatment. The term "in need" is meant to include both pharmaceutical or health-related needs, for example, treating hyperhidrosis, acne or other conditions involving the excess production of secretions or sweat. In general the compositions are prepared by mixing the oligopeptide with the carrier, and usually with one or more additional pharmaceutically acceptable carriers or excipients. In their simplest form they may contain a simple aqueous pharmaceutically acceptable carrier or diluent, such as buffered saline. However, the compositions may contain other ingredients typical in topical pharmaceutical or cosmeceutical compositions, that is, a dermatologically or pharmaceutically acceptable carrier, vehicle or medium, i.e. a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. As appropriate, compositions of the invention may comprise any ingredient conventionally used in the fields under consideration, and particularly in cosmetics and dermatology. The compositions also may include a quantity of a small anion, preferably a polyvalent anion, for example, phosphate, aspartate, or citrate.

In terms of their form, compositions of this invention may include solutions, emulsions (including microemulsions), suspensions, creams, lotions, gels, powders, or other typical solid or liquid compositions used for application to skin and other tissues where the compositions may be used. Such compositions may contain, in addition to the oligopeptide and carrier, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

Compositions according to this invention may be in the form of controlled-release or sustained-release compositions, wherein the oligopeptide and the optional carrier are encapsulated or otherwise contained within a material such that they are released onto the skin in a controlled manner over time. The oligopeptide and optional carrier may be contained within matrixes, liposomes, vesicles, microcapsules, microspheres and the like, or within a solid particulate material, all of which is selected and/or constructed to provide release of the oligopeptide over time. The oligopeptide and the optional carrier may be encapsulated together (e.g., in the same capsule) or separately (in separate capsules).

In particular embodiments, the compositions include gelling agents and/or viscosity-modifying agents. These agents are generally added to increase the viscosity of the composition, so as to make the application of the composition easier and more accurate. Additionally, these agents help to prevent the aqueous oligopeptide/carrier solution from drying out, which tends to cause a decrease in the activity of the oligopeptide. Suitable agents are those that are uncharged and do not interfere with the oligopeptide activity or the efficiency of the oligopeptide-carrier complexes in crossing skin. The gelling agents may be certain cellulose-based gelling agents, such as hydroxypropylcellulose (HPC) for example. In some embodiments, the oligopeptide/carrier complex is formulated in a composition having 2-4% HPC. Alternatively, the viscosity of a solution containing a oligopeptide/carrier complex may be altered by adding polyethylene glycol (PEG). In other embodiments, the oligopeptide/carrier solution is combined with pre-mixed viscous agents, such as Cetaphil® moisturizer.

The compositions of this invention may optionally include partitioning agents. As used herein, a "partitioning agent" is any substance or additive that has the property of preventing or minimizing unwanted or uncontrolled aggregation of the oligopeptide with the carriers of this invention. Partitioning agents may be useful, for example, when a concentrated oligopeptide solution must be employed due to volume constraints. In these cases, the partitioning agent keeps the oligopeptide dispersed, thereby preventing aggregation of the oligopeptide that would otherwise occur without the partioning agent. Generally, a partitioning agent is (I) non-irritating, (2) does not destroy the oligopeptide, (3) does not confer any increase in permeability, (4) affords reliable and stable particle sizes. (5) is uncharged, and (6) does not interfere with complexes of the oligopeptide and the transdermal carrier. An example of a suitable partitioning agent is ethanol (EtOH). In some embodiments, the EtOH is less than 20% of the composition, and in other embodiments, less than 5% of the composition.

The oligopeptide can be delivered to glandular structures within the skin, in an effective amount to produce reduced glandular output, or other desired effects. Local delivery of the oligopeptide in this manner could afford dosage reductions, reduce toxicity and allow more precise dosage optimization for desired effects relative to injectable or implantable compositions. In the case of hyperhidrosis affecting the palm of the hand, the oligopeptide may be applied in conduction with a glove so that absorption of the oligopeptide is maximized.

The compositions of the invention are applied so as to administer an effective amount of the oligopeptide. The term "effective amount" as used herein means an amount of an oligopeptide as defined above that is sufficient to produce the desired reduction in synaptic transmission but that implicitly is a safe amount, i.e. one that is low enough to avoid serious side effects. Desired effects include but are not limited to relaxation of muscles, reduction of tremors and a reduction in the amount of glandular secretions produced. The compositions of the invention may contain an appropriate effective amount of the oligopeptide for application as a single-dose treatment, or may be more concentrated, either for dilution at the place of administration or for use in multiple applications. Through the use of the positively charged carriers of this invention, the oligopeptide can be administered transdermally to a subject for treating conditions such as hyperhidrosis or acne. The oligopeptide is administered topically for transdermal delivery to muscles or to other skin-associated structures. As non-limiting examples, the administration may be made, for example, to the legs, shoulders, back (including lower back), axilla, palms, feet, neck, groin, dorsa of the hands or feet, elbows, upper arms, knees, upper legs, buttocks, torso, pelvis, or any other part of the body where administration of the oligopeptide is desired.

The compositions are administered by or under the direction of a physician or other health care professional. They may be administered in a single treatment or in a series of periodic treatments over time. For transdermal delivery of the oligopeptide for the purposes mentioned above, a composition as described above is applied topically to the skin at a location or locations where the effect is desired. In embodiments were an aqueous oligopeptide solution is applied directly to the skin, it is preferable to cover the treated area (e.g., with Cetaphil® moisturizer) or occlude the treated area with a barrier (e.g., Telfa), in order to prevent the solution from drying out, which would lead to a decrease in oligopeptide activity. In some embodiments the amount of oligopeptide applied should be applied with care, at an application rate and frequency of application that will produce the desired result without producing any adverse or undesired results. Accordingly, for instance, topical compositions of the invention should be applied at a rate of from about 0.1 to about 800 µg, preferably from about 1.0 to about 50 µg oligopeptide per $cm^2$ of skin surface. Higher dosages within these ranges could be employed in conjunction with controlled release materials, for instance, or allowed a shorter dwell time on the skin prior to removal.

Proper preparation of the skin surface prior to the application of the oligopeptide composition is important for maintaining the efficacy of the solution. For example, the introduction of surfactants on the surface of the skin for the purpose of cleaning off surface oils on the skin prior to application is surprisingly counterproductive, because the surfactants appear to destroy the activity of the botulinum toxin. This occurs even if the skin is subsequently washed with water several times before application of the oligopeptide solution. Even extremely gentle surfactants, such as those found in baby wipes, appear to cause this phenomenon. Accordingly, in methods of administering the compositions of this invention, the skin is pre-cleaned using water alone. Washing with only water also appears to improve the transdermal transport of the botulinum toxin moderately.

Additionally, the skin may be stripped to reduce the stratum corneum layer prior to application of the oligopeptide complex. In principle, the process of stripping the skin should lead to enhanced efficiency of transdermal transport of the oligopeptide. However, the method used to strip the skin is important. For example, acetone-mediated reduction of the stratum corneum layer in humans or animals appears to reduce the activity of subsequently applied oligopeptide. In contrast, tape stripping (i.e., applying tape on the surface of the skin and then removing the tape) appears to allow deeper penetration of the oligopeptide and dosage reduction. It is presumed that abrasion of the skin surface (e.g., via the use of abrasive pads) would cause a similar effect as tape stripping.

This invention also comprises devices for transdermal transmission of an oligopeptide that contain a composition that in turn comprises a carrier that has a positively charged backbone with attached branching groups as defined herein, and an oligopeptide. Such devices may be as simple in construction as a skin patch, or may be a more complicated device that includes means for dispensing and monitoring the dispensing of the composition, and optionally means for monitoring the condition of the subject in one or more aspects, including monitoring the reaction of the subject to the substances being dispensed.

The compositions, both in general, and in such devices, can be pre-formulated or pre-installed in the device as such, or can be prepared later, for example using a kit that contains the two ingredients (oligopeptide and optional carrier) for combining at or prior to the time of application. The amount of carrier molecule or the ratio of it to the oligopeptide will depend on which carrier is chosen for use in the composition in question. The appropriate amount or ratio of carrier molecule in a given case can readily be determined, for example, by conducting one or more experiments such as those described below.

In general, the invention also comprises a method for administering oligopeptide to a subject or patient in need thereof, comprising topically administering an effective amount of the oligopeptide optionally in conjunction with a carrier comprising a positively charged backbone with attached positively charged branching groups, as described herein. By "in conjunction with" is meant that the two components (oligopeptide and carrier) are administered in a combination procedure, which may involve either combining them in a composition, which is then administered to the subject, or administering them separately, but in a manner such that they act together to provide the requisite delivery of an effective amount of the therapeutic protein. For example, a composition containing the carrier may first be applied to the skin of the subject, followed by applying a skin patch or other device containing the oligopeptide. The oligopeptide may be incorporated in dry form in a skin patch or other dispensing device and the positively charged carrier may be applied to the skin surface before application of the patch so that the two act together, resulting in the desired transdermal delivery. In that sense, thus, the two substances (carrier and oligopeptide) act in combination or perhaps interact to form a composition or combination in situ. Accordingly, the invention also comprises a kit that includes both a device for dispensing oligopeptide via the skin and a liquid, gel, cream or the like that contains the carrier or backbone, and that is suitable for applying to the skin or epithelium of a subject. Kits for administering the compositions of the inventions, either under direction of a health care professional or by the patient or subject, may also include a custom applicator suitable for that purpose.

The compositions, kits and methods of this invention allow for the delivery of a more pure oligopeptide with higher specific activity and potentially improved pharmacokinetics. In addition, the carrier can act as a stabilizer, reducing the need for foreign accessory proteins (e.g., human serum albumin ranging from 400-600 mg or recombinant serum albumin ranging from 250-500 mg) and/or polysaccharide stabilizers, and can afford beneficial reductions in immune responses to the oligopeptide. In addition, the compositions are suitable for use in physiologic environments with pH ranging from about 4.5 to about 6.3, and may thus have such a pH. The compositions according to this invention may be stored either at room temperature or under refrigerated conditions.

The following are non-limiting representative examples of implementations of the invention. They demonstrate the delivery of a functional oligopeptide across skin without requiring covalent modification of the oligopeptide, the ability of the oligopeptide to reduce the production of sweat and the ability of the oligopeptide to reduce the strength of muscle contractions.

Example 1

Inhibition of Sweat by BOTOX® and the Oligopeptide EEMQRR (SEQ ID NO: 1) in a Mouse Hind Foot Model Methods:

A pilocarpine solution and rodent anesthetic were prepared 24 hours prior to treatment of the animals. The pilocarpine solution was made at a concentration of 1 mg/ml in 0.9% NaCl in a 15-ml centrifuge tube. The solution was vortexed to mix well for 2 minutes and then sterilized by filtering through a PURADISC 25 TF disposable filter device into a sterile vial. The pilocarpine solution was then covered with foil. The rodent anesthetic cocktail was prepared by combining 3.75 ml of 100 mg/ml Ketamine, 3.00 ml of 20 mg/ml Xulazine, and 23.25 ml of saline and vortexing well to mix.

A 2% iodine solution was prepared in 70% ethanol in a 50-ml centrifuge tube by vortexing to mix well followed by sonication for 15 minutes and then vortexing again. The tube was then covered with parafilm.

The lysine-asparagine-arginine (KNR) backbone and lysine-asparagine-threonine (KNT) backbone were prepared as a 1 mg/ml solution in deionized $H_2O$. BOTOX® (botulinum toxin type A; Allergan Inc., Irvine Calif.) was reconstituted in 1.0 ml of 0.9% sodium chloride at a concentration of 100 units/ml. The oligopeptide EEMQRR (SEQ ID NO: 1) was prepared in deionized $H_2O$ at a concentration of 1 mg/ml.

There were 6 experimental groups in the study:
BO: null+BOTOX®
BP: KNT+BOTOX®
BQ: KNT+BOTOX®
BR: null+Oligopeptide EEMQRR (SEQ ID NO: 1)
BS: KNR+Oligopeptide EEMQRR (SEQ ID NO: 1)
BT: KNT+Oligopeptide EEMQRR (SEQ ID NO: 1)

The stock solutions for treatment of each of the groups were prepared as follows:
BO: 70 µl BOTOX® and 70 µl PBS.
BP: 70 µl BOTOX®, 35 µl KNR backbone and 35 µl PBS.
BQ: 70 µl BOTOX®, 35 µl KNT backbone and 35 µl PBS.
BR: 70 µl oligopeptide EEMQRR (SEQ ID NO: 1) and 70 µl PBS.
BS: 70 µl oligopeptide EEMQRR (SEQ ID NO: 1), 35 µl KNR backbone and 35 µl PBS.
BT: 70 µl oligopeptide EEMQRR (SEQ ID NO: 1), 35 µl KNT backbone and 35 µl PBS.

Groups: 6 paws per group, except BQ and BT which have 5 paws per group.

Study Procedure:

1. Animals were anesthetized with 0.07 ml of anesthetic cocktail injected intraperitoneally and supplemented with isoflurane as necessary.

2. A total of 20 µl of each treatment solution was applied topically to the assigned hind feet. A pipet tip was used to rub the treatment solution into the hind feet and to coat the bottom of the hind feet completely. The animals' right hind feet received the Botox treatments and the animals' left hind feet received the oligopeptide EEMQRR (SEQ ID NO: 1) treatments.

3. To dry the treatment solution, the animals were placed under a heat lamp for two minutes and then the feet air dried for 5 minutes.

4. Step 2-3 were repeated until all of the treatment solution had been applied and absorbed by the animals' hind feet. Typically this was achieved with two 10 µl applications.

5. After the treatment solution had dried completely, approximately 50 µl of Cetaphil® (k cream was applied to the hind feet.

6. The animals' vital signs were monitored until they recovered from the anesthetic.

After one week, sweat production was evaluated by the use of the starch iodide test. The starch iodide test was carried out by the following procedure.

1. The animals were anesthetized with 0.07 ml of anesthetic cocktail injected intraperitoneally supplemented with isoflurane as necessary. If booster dose was necessary, 0.03 ml of anesthetic cocktail was given.

3. After 10 minutes when the animals were fully anesthetized and had stable vital signs, both hind feet were painted with a 2% iodine solution in ethanol.

4. To dry the feet, the animals were placed under a heat lamp for two minutes and then the feet air dried for 5 minutes.

5. The iodine coated feet were then photographed.

6. To induce secretion of sweat, the animals were injected with 0.10 ml of 1 mg/ml pilocarpine HCl in 0.9% sodium chloride intraperitoneally. This injection was done about 30 minutes after injection of the anesthetic cocktail.

7. The hind feet were then completely coated with starch powder which was rubbed into the feed with fingers wearing powder-free gloves. Excess starch was removed with a small paint brush. Starch was then loosely applied with a compact velour pad. This step was then repeated leaving a light powder residue on the hind feet. Gloves were changed for each treatment group.

8. Observed the mice for urine and other secretions. Do not let urine come in contact with the animals' hind feet. Keep the animals on a dry surface.

9. Took pictures of hind feet (to record blue-black positive spots) at 10, 20 and 60 minutes after pilocarpine injection.

10. Monitored vitals and waited for recovery.

Figure 1:
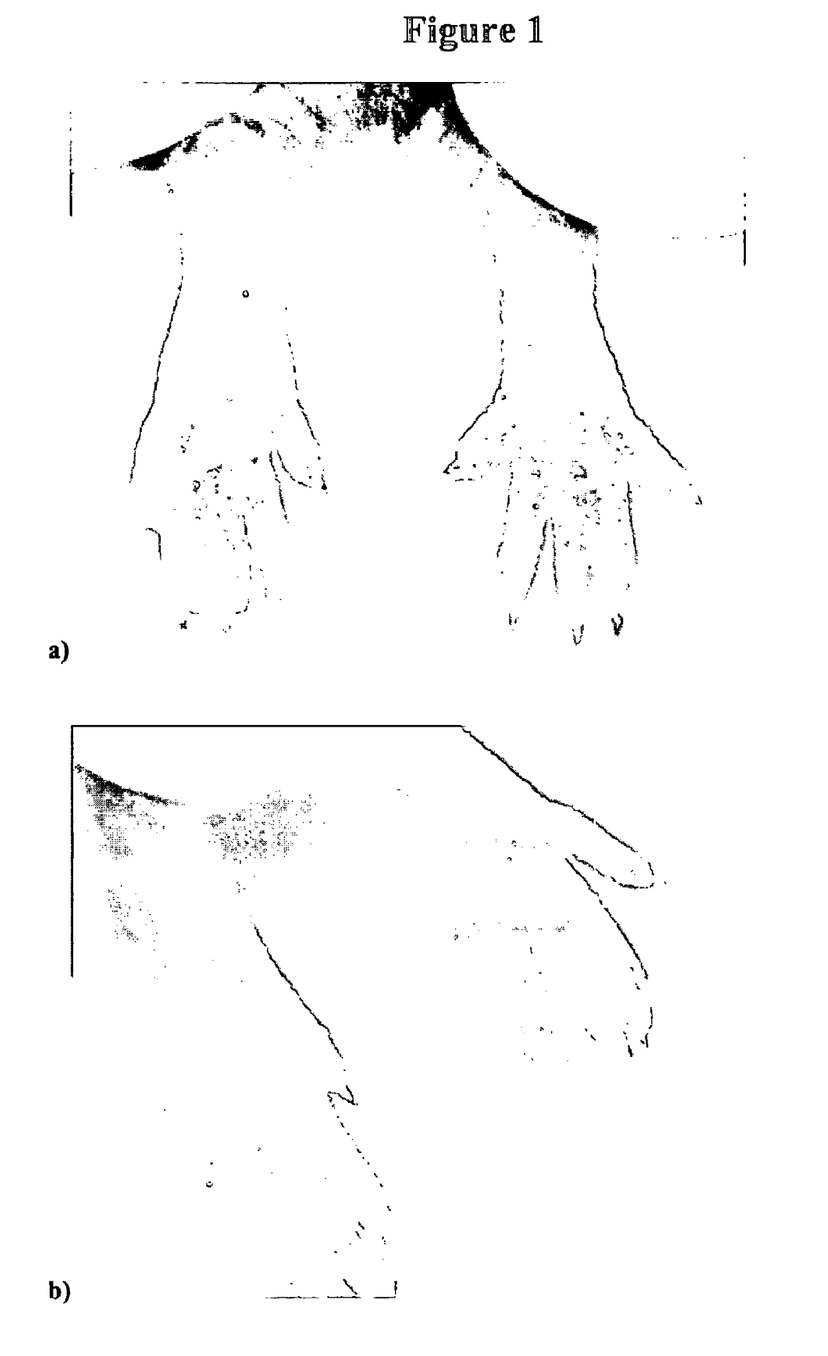
FIG. 1 is a series of photographs depicting mouse foot sweat production visualized by iodine-starch staining, (blue-black positives) 7 days after topical application of oligopeptide EEMQRR (SEQ ID NO: 1) (left foot) or botulinum toxin (right foot) without carrier (a and c) or oligopeptide EEMQRR (SEQ ID NO: 1) (left foot) or botulinum toxin (right foot) with KNR (b and d) in two different animals.

Observations and Results: The blue-black positive spots were typically best viewed at 50-60 minutes after pilocarpine injection. The starch-iodine test showed that the treatment groups had less blue-black positive spots than the control for both treatments as depicted in the attached representative photographs. Oligopeptide EEMQRR (SEQ ID NO: 1) plus a transporter functions markedly better than oligopeptide EEMQRR (SEQ ID NO: 1) alone. Oligopeptide EEMQRR (SEQ ID NO: 1) alone is marginally better than Botox alone. Thus surprisingly (1) an oligopeptide can interfere with a secretory condition when applied topically, (2) this process essentially requires a transdermal transport enhancer for therapeutic effects, and (3) these effects can approximate those of native intact botulinum toxin with a suitable transdermal transport enhancer in this model.

Example 2

Topical Application of Oligopeptide EEMORR (SEQ ID NO: 1) to Treat Axillary Hyperhidrosis in a Human Patient Methods:

Participants in the study had pre-existing, subjective hyperhidrosis of the axilla prior to entry in the study. The axilla sweating by gravimetric measurement exceeded 50 mg/5 minutes in both arms. Subjects were 18 years or older, healthy, and with no concurrent treatment with anticholinergic or aminoglycoside or calcium channel blocker (60 days wash off time).

Gravimetric Measurement:
Acclimation and Dose Area Preparation:

The patient was acclimated for 15 minutes at a room temperature of 72~77 oF at the resting position. The patient removed all shirts exposing both axillae. The dose area which covered 1 cm beyond the hair bearing skin at each axilla was mapped. The dose area was washed with pre-wet sterile gauze pad from a 50 ml conical tube with 5 long strokes from top to bottom in the same direction using one side of the gauze. This wash step was repeated three more times. The axilla was dried with a dry sterile gauze firm padding motion from top to bottom of the axilla then further dried by placing a filter paper under the axillary crease and allowed the filter paper to dwell in the test site for 5 minutes. The patient sat with his arms against their bodies in a resting position. The patient was at rest for 1 minute without axilla manipulation prior to the first gravimetric assessment.

Sweat Production Measurement (Gravimetric Measurement):

The patient held hands together at the back of head to fully expose axilla while being reclined in a 45 degree angle. The pre-weighed filter paper was removed from the conical tube and place it under the patient's axilla with the tip of the filter aligns with the center of axilla crease line. The patient relaxed his arms to the side of the bodies and sat with both arms held tightly against his trunk. The clock started when the filter papers are securely placed under both of the axillae. The two axillae were measured simultaneously. After 5 minutes, the filter papers were removed from the axillae and placed each one into the same respective conical tubes and the caps were screwed tightly to prevent the evaporation of the sweat from the tube. Sweat production was repeated two more times at 1 minute intervals.

Starch/Iodine Test:

The patient held hands together at the back of head to fully expose axilla. Iodine solution was applied to the axilla area with a sterile gauze pad and then air dried completely. The area covered by iodine was padded with a thin layer of starch using cotton balls. The patient sat with both arms held tightly against his trunk. After 5 minutes, the patient raised the arms and held hands together at the back of head to fully expose axillae. Baseline and post starch-iodine pictures of left and right axilla were taken. The axillae were cleaned first with 70% EtOH and then with sterile DI water.

Treatment Formulation and Application:
Formulations:
1st Treatment:

Left arm: 600 µl of KN-T (1 mg/ml in saline and 1% EtOH) was added to 600 µl of oligopeptide EEMQRR (SEQ ID NO: 1) (10% in saline, plus 1% EtOH), mixed by inversion; the mixture sat at room temperature for 5 minutes. Added 600 µl of 4% HPC (1% EtOH) and mixed thoroughly. Transferred the homogenous solution into a 3 ml syringe.

Right arm: 600 μl of KN-T (1 mg/ml in saline and 1% EtOH) was added to 600 μl of saline (with 1% EtOH), mixed by inversion; the mixture sat at room temperature for 5 minutes. Added 600 μl of 4% HPC (1% EtOH) to the mixture and mixed thoroughly. Transferred the homogenous solution into a 3 ml syringe.

2nd Treatment:

Left arm: 500 μl of KN-T (1 mg/ml in saline and 5% EtOH) was added to 500 μl of tetra-aspartate-oligopeptide EEMQRR (SEQ ID NO: 1) (10% in saline and 5% EtOH), mixed by inversion; the mixture sat at room temperature for 5 minutes. Added 500 μl of 4% HPC (1% EtOH) and mixed thoroughly. Transferred the homogenous solution into a 3 ml syringe.

Right arm: 500 μl of KN-T (1 mg/ml in saline and 5% EtOH) was added to 500 μl of saline (with 5% EtOH), mixed by inversion; the mixture sat at room temperature for 5 minutes. Added 500 μl of 4% HPC (1% EtOH) to the mixture and mixed thoroughly. Transferred the homogenous solution into a 3 ml syringe.

Results:

TABLE 1

Formulation summary (Left arm only)

|  | 10% oligopeptide EEMQRR (SEQ ID NO: 1) (saline) | Carrier (1 mg/ml) | HPC (4%) | EtOH |
|---|---|---|---|---|
| 1st treatment | 600 μl oligopeptide EEMQRR (SEQ ID NO: 1) | 600 μl KN-T | 600 μl | 1% |
| 2nd treatment | 500 μl tetra-asp-oligopeptide EEMQRR (SEQ ID NO: 1) | 500 μl KN-T | 500 μl | 5% |

Example 3

Topical Application Revance Carrier and D10, SNARE-Disrupting Oligopeptide Complex, on Muscle Force Generation in a Mouse Model Drug Application:

While wearing sterile gloves, the drug was spread with syringe evenly around the dose site and massaged with fingers for 1 minute. The patient put his arms down along the side of the body and incubated for 1 hour. At the end of incubation, the dose site was cleansed with sterile gauze.

Results

TABLE 2

Study Summary
(Gravimetric measurement (milligram/5 minutes))

| ID | Baseline | 2 week post treatment | 1st Treatment | Randomization |
|---|---|---|---|---|
| Left | 371.0 +/− 35.8 (435.0) | 35.6 +/− 12.3 (60.0) | oligo/KN-T/HPC/1% EtOH | Oligopeptide EEMQRR (SEQ ID NO: 1) |
| Right | 291.7 +/− 26.4 (320.5) | 20.1 +/− 7.3 (32.4) | Saline/KN-T/HPC/1% EtOH | Control |
| Ratio (Left/right) | 1.3 | 1.8 | | |

| ID | Baseline 2nd treatment | 3 week/ 1 week post RT | 4 week/ 2 week post RT | 2nd treatment | Randomization |
|---|---|---|---|---|---|
| Left-2 | 35.6 +/− 12.3 (60.0) | 53.8 +/− 3.5 (60.0) | 54.2 +/− 2.9 (58.7) | Tetra-Asp-oligo/KN-T/HPC/1% EtOH | Oligopeptide EEMQRR (SEQ ID NO: 1) |
| Right-2 | 20.1 +/− 7.3 (32.4) | 47.1 +/− 6.5 (54.0) | 44.6 +/− 3.1 (50.8) | Saline/KN-T/HPC/1% EtOH | Control |
| Ratio (left/right) | 1.8 | 1.1 | 1.2 | | |

Example 3

Topical Application Revance Carrier and D10, SNARE-Disrupting Olilopeptide Complex, on Muscle Force Generation in a Mouse Model Materials and Methods:

D10 (modified acetyl hexapeptide, Revance Therapeutics, Mountain View, Calif.)

Polylysine Peptides (Carriers): Kn21T

Test Groups:

|  | Kn21T carrier | No carrier |
|---|---|---|
| 10% D10 | x | |
| Control | | x |

Study Design:

Male CD1 mice (Charles River, Wilmington, Mass.) weighing 27-33 g were used. Mice were housed in groups of 5 and allowed ad libitum access to food and water before treatment. Animals were anesthetized using 1.5% isoflurane mixed with oxygen and remained anesthetized for the duration of the study. A dose site of each mouse's hind limb was carefully shaved with an Andis Edjer II cordless rechargeable trimmer (Andis, Sturtevant, Wis.). The dosing site was prepared with an acetone wash or DI water wash. The dosing site was dried completely before treatment application. Untreated normals, as well as those treated with base formulations (no toxin) applied topically at an equivalent volume served as controls. Muscle contraction force was measured at 2-3.5 hours post topical treatment.

D10 (Modified Acetyl Hexapeptide) Preparation:
1. Made a 1.0 mg/ml stock solution of Kn21T carrier with 0.9% NaCl and 5% EtOH in a microcentrifuge tube and mixed by vortex.
2. Made a 10% D10 solution in a centrifuge tube and mixed by vortex.
3. Took 100 µl of carrier from step 1 and added it to 100 µl of 10% D10 from step 2 into a microcentrifuge tube and the mixture sat at room temperature for 5 minutes with the tube standing upright for the complexes to form, and then gently inverted again before dosing.
4. Removed 200 µl of the mixture from step 3 with a pipet and applied it to the hind leg.

Topical Application:
1. Anesthetized the mouse with 1.5% isoflurane mixed with oxygen.
2. Slowly applied the carrier/toxin mixture by using a pipet to spread to the hind leg of the mouse (shaved), massaged the mixture onto the right hind leg while wearing nitrile gloves, incubated for 30 minutes while the mouse is under anesthesia, then the animal was allowed to recover to observe foot mobility (DAS). The animal was placed under anesthesia again until muscle force generation test that took place 2 to 3.5 hours post treatment.
a. There was no direct heat-lamp exposure hind limb after topical application during 30-minute dwell time.

Muscle Contraction Force Generation:
The limb was immobilized by securing it to a wooden table using K-wires through the femur and the tibia to prevent motion. The gastrocnemius was left in situ. A wire suture was tied around the distal end of the Achilles tendon. The tendon was then transected distal to the suture, and the suture was attached to a force transducer (model FT03, Grass, West Warwick, R.I.), which in turn was connected to a force transducer amplifier (model 13-G4615-50, Gould, Cleveland, Ohio). The sciatic nerve from the D10 treated side was stimulated directly (SD9 stimulator, Grass, West Warwick, R1) with increasing voltage until the maximum isometric single-twitch force was obtained. The frequency of stimulation then was increased until maximum tetanic force was generated. Twitch is generated by stimulation of one motor unit, and tetanus is generated by applying summation of all motor units by supermaximal stimulation. The same procedure was repeated on the control limbs. Responses were recorded with a calibrated recording oscillation (RS 3800, Gould, Cleveland, Ohio) linked to the force transducer. [Ma J. Elsaidi G A, Smith T L, et al. Time course of recovery of juvenile skeletal muscle after botulinum toxin A injection. Am. J. Phys. Med. Rehabil. 2004; 83(10):774-780].

Results
Normal values of muscle force generation in a C57BL/6 mice has a mean single twitch force of 60±15 grams and a mean tetanus force of 240±30 grams in a previous study with injection of botulinum toxin A. In this pilot preclinical study, comparable mean single twitch force of 54±2 grams and mean tetanus force of 241±20 grams were found.

When muscle force generation of topical D10 with carrier was evaluated, it showed a small response resulting in approximately 56% decrease in single twitch and 37% decrease in tetanus response in animal treated with single-time administration of topical "Revance D10 solution" with carrier versus the controls on the recordings. Table 3 shows the summary of mean muscle force generation and percentage of decrease for single twitch and tetanus.

TABLE 3

Summary of muscle force generation. Mean values and % of decrease for treatment group versus control are presented.

| Treatment | Carrier | Muscle Force Generation | Mean Results (g) | Mean % decrease |
|---|---|---|---|---|
| D10 | Kn21T | single twitch | 20 | 56% |
|  |  | tetanus | 132 | 37% |
| Control | N/A | single twitch | 45* | 0% |
|  |  | tetanus | 210* | 0% |

*lower limit

CONCLUSION

This study serves to demonstrate that topical application of 10% D10 per mouse limb can effectively decrease motor force generation and shows evidence of therapeutic benefits.

What is claimed is:

1. A topical composition, comprising:
   an optionally derivatized oligopeptide of from 6 to 20 amino acids comprising the amino acid sequence of SEQ ID NO: 1 wherein the oligopeptide is not covalently bonded to a carrier; and
   a positively charged polylysine carrier comprising positively charged branching groups selected from the group consisting of $(gly)_p$-RGRDDRRQRRR-$(gly)_q$ SEQ ID NO: 5, $(gly)_p$-YGRKKRRQRRR-$(gly)_q$ SEQ ID NO: 6, and $(gly)_p$-RKKRRQRRR-$(gly)_q$ SEQ ID NO: 7, wherein the subscripts p and q are each independently an integer of from 0 to 20,
   wherein the oligopeptide and the positively charged polylysine carrier are non-covalently associated.

2. The composition according to claim 1 wherein the oligopeptide is derivatized.

3. The composition according to claim 2 wherein the oligopeptide is derivatized with an acetyl group or a palmitoyl group.

4. The composition according to claim 1 wherein the oligopeptide is recombinantly produced.

5. The composition according to claim 1 wherein the composition is a cream, lotion, ointment, gel or liquid.

6. The composition according to claim 5 wherein the composition further comprises a buffer.

7. The composition according to claim 1 wherein the composition is a controlled release composition.

8. The composition according to claim 1 wherein the composition further comprises saline.

9. The composition according to claim 8 wherein the composition further comprises a buffer.

10. The composition according to claim 1 in which the positively charged branching groups comprise at least about 0.05% by weight of the total carrier weight.

11. The composition according to claim 1 in which the positively charged branching groups comprise from about 0.5% to about 45% by weight of the total carrier weight.

12. The composition according to claim 1 in which the positively charged branching groups comprise from about 0.1% to about 30% by weight of the total carrier weight.

13. The composition according to claim 1 in which the polylysine has a molecular weight of from about 10,000 to 1,500,000.

14. The composition according to claim 1 in which the polylysine has a molecular weight of from about 25,000 to about 1,200,000.

15. The composition according to claim 1 in which the polylysine has a molecular weight of from about 100,000 to about 1,000,000.

16. A kit for topically administering to a subject an effective amount of an optionally derivatized oligopeptide of from 6-20 amino acids comprising the amino acid sequence of SEQ ID NO: 1, the kit comprising the optionally derivatized oligopeptide, wherein the oligopeptide is not covalently bonded to a carrier; and
    a positively charged polylysine carrier comprising positively charged branching groups selected form the group consisting of $(gly)_p$-RGRDDRRQRRR-$(gly)_q$ SEQ ID NO: 5, $(gly)_p$-YGRKKRRQRRR-$(gly)_q$ SEQ ID NO: 6, and $(gly)_p$-RKKRRQRRR-$(gly)_q$ SEQ ID NO: 7, wherein the subscripts p and q are each independently an integer of from 0 to 20,
    wherein the oligopeptide and the positively charged polylysine carrier are non-covalently associated.

17. The kit according to claim 16 further comprising a custom applicator.

18. The kit according to claim 17 in which the custom applicator is designed for use by a health care professional.

19. The kit according to claim 17 in which the custom applicator is designed for self-administration by a subject.

20. The kit according to claim 16, wherein the oligopeptide and the positively charged polylysine carrier are provided as a pre-formulated composition.

21. The kit according to claim 16, wherein the oligopeptide and the positively charged polylysine carrier are provided separately for combining prior to administration.

22. The kit according to claim 17, wherein the oligopeptide and the positively charged polylysine carrier are contained in the custom applicator.

23. The kit according to claim 22, wherein the custom applicator is a skin patch.

24. The composition according to claim 1, wherein the optionally derivatized oligopeptide contains 3-14 neutral or non-polar amino acids.

25. The composition according to claim 1, wherein the optionally derivatized oligopeptide contains 3-14 acidic, negatively charged amino acids.

26. The composition according to claim 25, wherein the optionally derivatized oligopeptide is SEQ ID NO: 2 or SEQ ID NO: 3.

* * * * *